United States Patent [19]

Simpkins, Sr. et al.

[11] Patent Number: 5,274,851
[45] Date of Patent: Jan. 4, 1994

[54] PROTECTIVE GARMENT WITH A RESILIENT SUPPORT

[75] Inventors: Terry Simpkins, Sr.; Simpkins, Jr. Terry, both of Carlsbad; Robert M. King, Vista, all of Calif.

[73] Assignee: E-Z-EM, Inc., Westbury, N.Y.

[21] Appl. No.: 825,990

[22] Filed: Jan. 27, 1992

[51] Int. Cl.⁵ .......................... A41D 1/04; A61F 5/02
[52] U.S. Cl. .................................... 2/102; 2/44;
  2/92; 2/2; 2/108; 2/901; 2/915; 128/874
[58] Field of Search .................. 2/102, 44, 92, 2, 108,
  2/220, 236, DIG.; 128/78, 874; 250/516.1, 519.1

[56] References Cited

U.S. PATENT DOCUMENTS

| | | | |
|---|---|---|---|
| 2,300,306 | 10/1942 | Nagel | 2/102 |
| 2,404,225 | 7/1946 | Green | 250/516.1 |
| 3,052,799 | 9/1962 | Hollands | 250/516.1 |
| 3,093,829 | 6/1963 | Maine | 250/516.1 |
| 3,996,620 | 12/1976 | Maine | 2/2 |
| 4,441,025 | 4/1984 | McCoy | 250/516.1 |
| 4,494,546 | 1/1985 | Steiman | 2/67 |
| 4,602,386 | 7/1986 | Hoffman et al. | 2/2 |
| 4,766,608 | 8/1988 | Cusick et al. | 2/2 |
| 4,843,641 | 7/1989 | Cusick et al. | 2/2 |
| 5,007,412 | 4/1991 | Dewall | 2/102 |
| 5,015,865 | 5/1991 | Sayers | 250/516.1 |
| 5,077,837 | 1/1992 | Meistrell | 2/22 |

FOREIGN PATENT DOCUMENTS 2216227 8/1973 Fed. Rep. of Germany .......... 2/102
569317 1/1924 France ................................ 2/102

Primary Examiner—Clifford D. Crowder
Assistant Examiner—Gloria Hale
Attorney, Agent, or Firm—McAulay Fisher Nissen Goldberg & Kiel

[57] ABSTRACT

A protective garment incorporating radiation resistant materials has a resilient support for conforming to and supporting the weight of the garment across the back of the wearer. The support is a wide resilient band having a first end connected at a first interior side seam and a second end connected at a second interior side seam for extending across an interior back panel surface of the garment. When stretched across the back, the garment weight is distributed uniformly across the back to reduce fatigue. Alternatively, the garment may have a pair of resilient straps which extend from the shoulder seams and sides of a front panel, across the back to the front of the garment. By providing resilient back panels which extend from the shoulders, the front panel weight is distributed over the shoulders and back. Utilizing such a protective garment reduces upper body fatigue for those required to wear such garments.

12 Claims, 2 Drawing Sheets

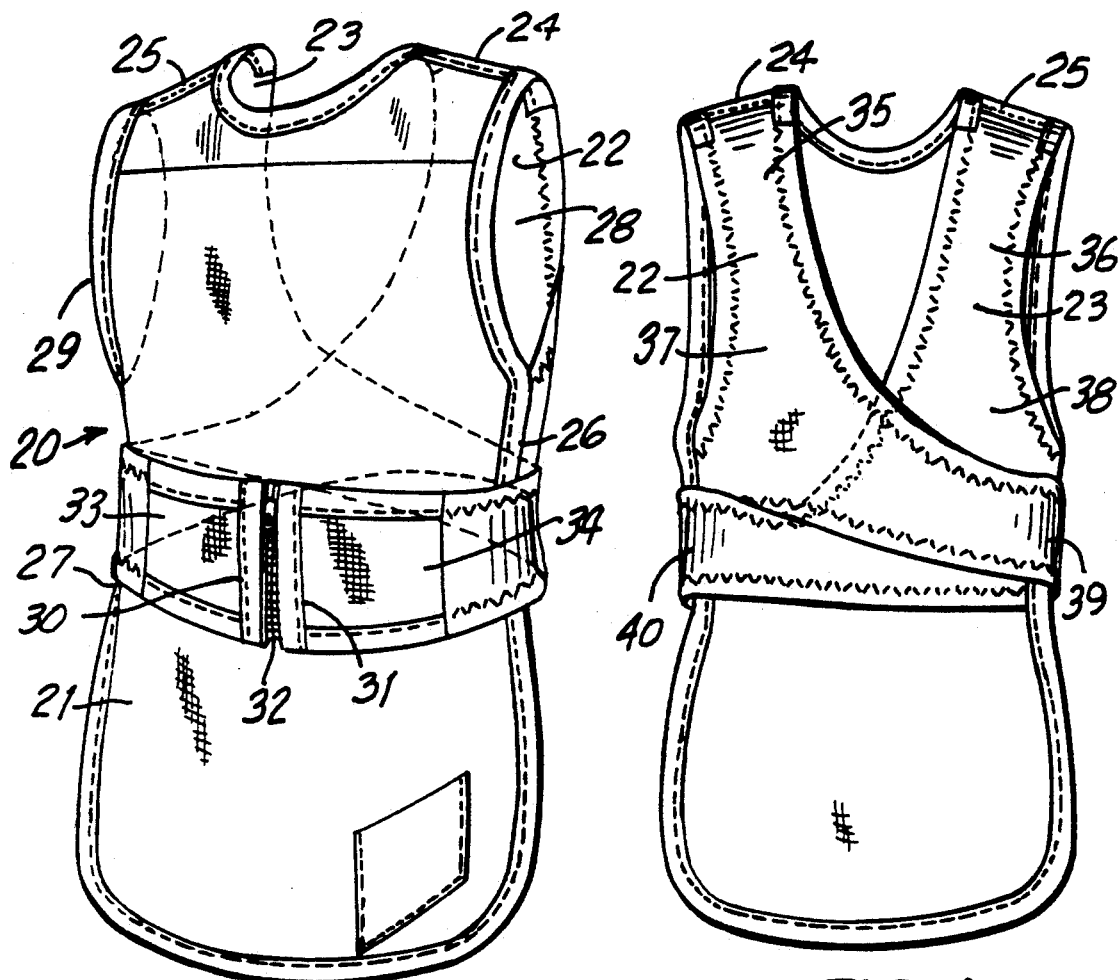
FIG.3
FIG.4
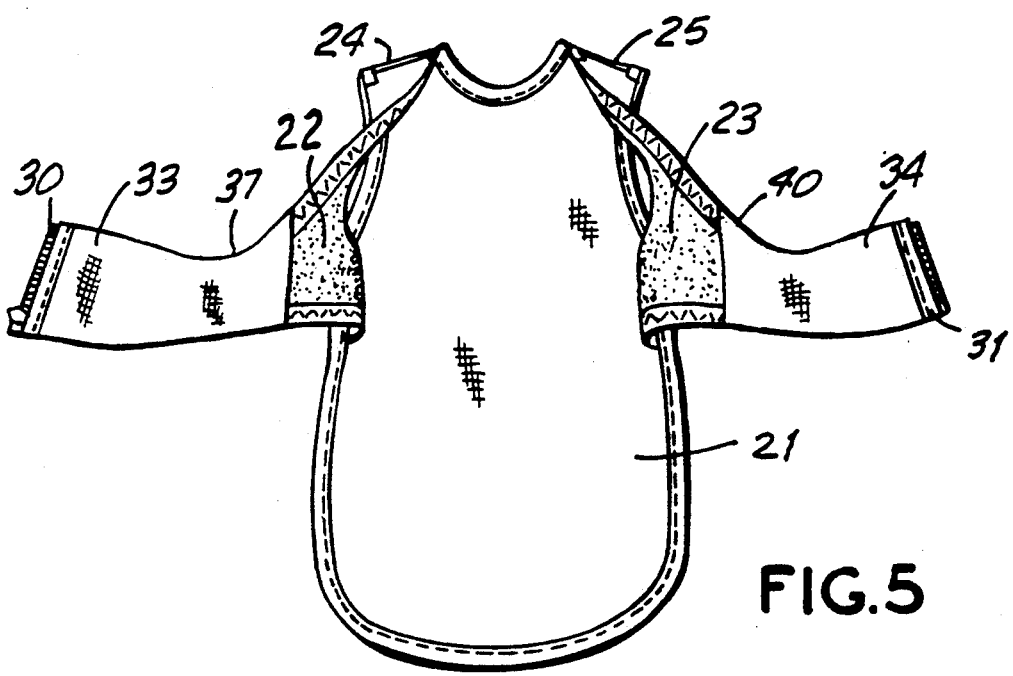
FIG.5

PROTECTIVE GARMENT WITH A RESILIENT SUPPORT

TECHNICAL FIELD

This invention relates to protective garments for use in or near a radiation environment and more particularly to a protective garment having resilient support means for reducing upper body fatigue for the person wearing the garment.

BACKGROUND

Protective garments for use by persons subject to potential exposure to radioactive energy are known. Such garments typically have inner and outer linings with an intermediate layer of lead which is impermeable to such rays. Due to the amount of lead utilized, such garments are quite heavy and can cause fatigue to the wearer through prolonged use.

In U.S. Pat. No. 4,441,025, a radiation shield construction has a front apron with shoulder straps and wing panels to distribute the weight of the front panel across the shoulders of the wearer. The inventor attempted to minimize fatigue by using crossing flaps in a lower region of the users back to distribute the weight. However, a significant portion of the weight is still carried by the shoulders.

In U.S. Pat. No. 4,766,608, a radiation shield garment has an elasticized belt arranged to be fastened around the exterior of the garment at waist level. The belt is stretched, tightened and secured around the waist to transfer a portion of the garment weight to the waist. However, a significant part of the weight is still concentrated on the shoulders and upper back.

SUMMARY OF THE INVENTION

It is an object of the present invention to provide a protective garment which adjusts the weight distribution of the garment to reduce fatigue.

It is another object to provide a protective garment which has means to distribute the garment weight across a wide portion of the shoulders and lower back.

These and other objects to the present invention are achieved by providing a radiology protective garment comprising a wide support member having at least a portion extending across the back of the garment. The support member is placed across the back and is resilient in orthogonal directions to conform to the three-dimensional contour of the small of the back of the garment wearer. In one embodiment, the support is attached at the ends thereof to the side edges of the back panel, the back support being stretched across the back when the front portions are attached.

In another embodiment, the protective garment comprises a front panel having resilient shoulder strap means, the shoulder strap means having a first shoulder strap with an end attached to a lower side of the front panel and a fastening end disposable about the front panel, a second shoulder strap having an end attached to a lower side of the front panel and a fastening end disposable about the front panel, for attachment to the first strap attaching end. The first and second straps are resiliently extensible in the portions contacting the back in at least two directions for spreading the weight of the garment over the back. The front panel drapes over the body, with the attached straps holding the panel against the stomach.

By making portions of the straps of a resilient material, the weight which was previously borne by the shoulders is distributed rather than concentrated over the shoulders and back. The garment weight is carried by the shoulders and back but in a way which enhances comfort. The attachment ends of the straps extend around the waist to hold the front panel against the body. Such protective garments are more easily carried and reduce upper body fatigue while increasing support for the lower back by distributing the weight of the garment over the shoulders and back.

BRIEF DESCRIPTION OF THE DRAWINGS

FIG. 3 is a front view of another embodiment of the protective garment of the present invention.

FIG. 4 is a rear view of the garment of FIG. 3.

FIG. 5 is a open view of the garment of FIG. 3.

DETAILED DESCRIPTION OF THE INVENTION

Figure 1:
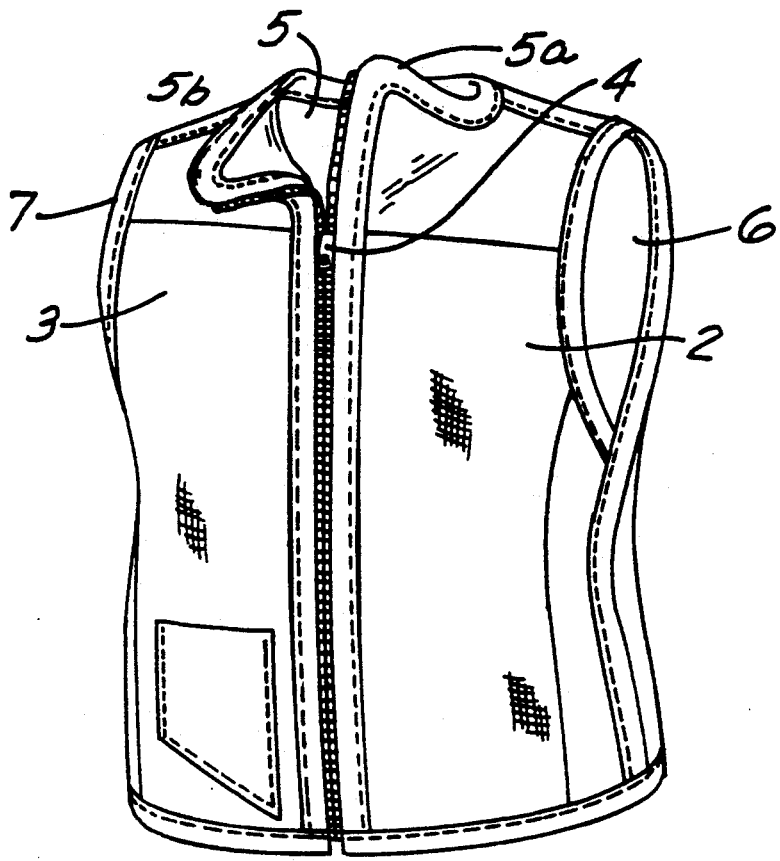
FIG. 1 is a front view of the protective garment of the present invention.

Referring to FIG. 1, a protective garment 1 has first and second front panels 2 and 3 respectively, connected by a releasable attachment mechanism 4 which in this case is a zipper. While a zipper is shown for attaching the front panels or straps together, it is believe that other attachment means, such as VELCRO separable fasteners could also be used. A zippered garment has the advantage of more freedom of movement and increased ventilation when partially zippered. Such a garment typically contains lead as a means for protecting the wearer of the garment from radiation energy. The garment has a neck opening 5 and arm openings 6 and 7. As shown, the garment optionally includes neck protecting portions 5a and 5b to cover the thyroid gland.

Figure 2:
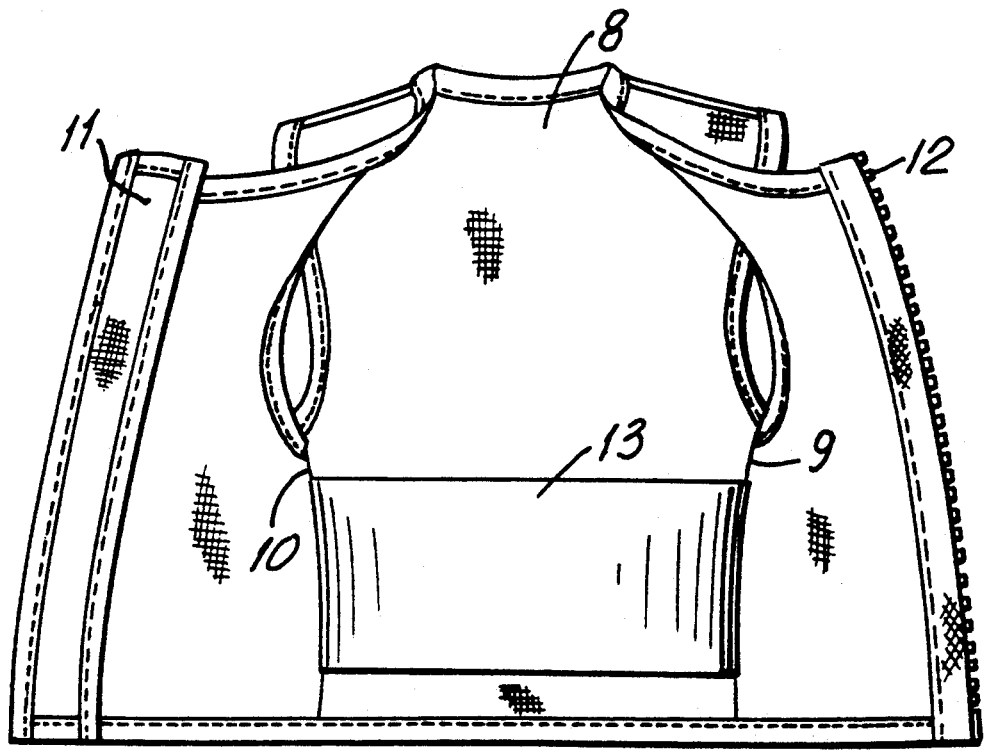
FIG. 2 is a view of an alternative embodiment of the garment of FIG. 1 shown with the front panels open.

Referring to FIG. 2, the garment 1, shown without the optional neck protecting portions, has a back panel 8 connected at seams 9 and 10 to the front panels. The front panel 3 has a strip 11 disposed behind a zipper portion (not shown), for attachment to a zipper portion 12 attached to the front panel 4. The back panel may also include shielding material therein, but typically, the amount of shielding in the back area is less than in the front panels.

Referring still to FIG. 2, a resilient back support 13 is attached only at its ends to the seams 9 and 10. The support 13 is located adjacent the lower back area and has a horizontal length such that in its relaxed condition, it is shorter than the width of the back panel from seam to seam. The support has a width sufficient to cover the entire lower back area of the wearer, and is sufficiently resilient in at least the horizontal and vertical directions to conform in three dimensions to the curvature of the back. In this embodiment, the support is about 6" wide and in its relaxed state is about 13" long. The back panel width, seam to seam, is about 20". A support width of about 4–8 inches should be adequate to adapt the support to any body size. Preferably, the support edges have no hem to increase comfort when in contact with the body.

When the garment is applied to the body, the support is stretched across the lower back as the wearer closes the front panels. Consequently, when the front panels are attached, the back support is stretched to match the width of the back panel. As the support is only attached at the seams, this forces the support to conform to the body and draw the front panel into the stomach. At the same time by conforming to the lower back, an uplifting of the garment occurs which releases a portion of the weight from the shoulders. Also, this conformance provides some space between the support and the back panel to allow ventilation.

After the front panels are engaged, they are pulled to the body by the support with sufficient force such that the weight of the garment is spread across the stomach, waist and lower back, and is thus not carried entirely by the shoulders.

The support must be extendable in at least both the longitudinal direction and perpendicular thereto for the support to conform to the three dimensional contours of the lower back of the individual wearing the protective garment. The support is composed of a resilient elastic material, having comparable moduli of elasticity in at least two directions and preferably has a compressible surface to adaptively conform to the body shape. Preferably, neoprene produced in the form of an elastic fabric is used as neoprene has identical moduli of elasticity in two directions. A lamination of neoprene foam with nylon spandex on one or two sides may also be used. Neoprene has the additional advantage of not bunching when relaxed, and is smooth and compressible for comfort. It is also easy to clean. Of course, other resilient elastic materials could be used.

The front of the garment preferably includes 0.50 inch thick lead in the front panels and the back panel preferably has 0.125 inch thick lead enclosed therein. Additionally, the strip 11 disposed behind the zipper has a similar lead strip to insure continuous lead shielding across the front of the garment. For maximum effectiveness, the garment front and back panels should be tailored to give a fairly snug fit about the waist and thus assure proper conformance of the support to the body and increased comfort.

Referring to FIG. 3, a protective garment 20 has a front apron 21 containing lead shielding therein. The garment has two panels 22 and 23 which extend from shoulder seams 24 and 25. Each panel 22 and 23 are composed of a resilient elastic material. The panel are also attached along side seams 26 and 27 with the space between the shoulder seam and side seam attachment points defining arm openings 28 and 29.

Each panel has an attachment end 30 and 31 which incorporate means for attaching the two panels together over the front panel. In this case, a zipper assembly 32 is used. Adjacent the zipper 32 are two non-resilient portions 33 and 34 which have a length sufficient to extend from the panels over the sides to meet over the stomach. Consequently, the resilient material 22, 23 stretches across the lower back and to the shoulders, but not over the sides or stomach, in response to the weight of the garment. It is the resilient panels 22 and 23 which distribute the apron weight and increase comfort to the wearer. The zipper assembly 32 and non-resilient portions 33 and 34 assure that the front apron remains close to the body.

Referring to FIG. 4, the back of the garment is shown. The panels 22 and 23 have tapered shoulder portions 35 and 36, leading to wide portions 37 and 38, then tapering to non-resilient narrow portions 39 and 40 sized for snug fitting to the waist. The panels are entirely elastic and rigid seams are avoided to enhance comfort. Fig. 5 shows the garment in the open condition. When in such a condition, the resilient material 22 and 33 is relaxed and thus is shorter than is required when the garment is worn. Thus, to attach the panel ends at the front, the non-resillient portions are pulled together and zippered which places the resilient back material in tension. This assures a snug fit of the garment to the body, yet allows one size garment to fit persons of different shapes and sizes.

The tapered shoulder panels, being resilient, allow the weight of the front apron to drape over the chest. Thus, the weight of the front apron is somewhat released from the shoulders and distributed by the panels across the back. If non-resilient material were used, the weight of the apron would be concentrated to a substantial extent on the shoulders which would cause fatigue. The garment as described by the present invention substantially reduces fatigue as the weight which is carried by the shoulders is distributed over a wide area by the resilient panels crossing the back which further reduces discomfort and fatigue.

The resilient panels are made of the same resilient material as previously described, and are preferably made of neoprene. Similarly, the front apron is preferably composed of a material which incorporates about 0.5 inches of lead shielding therein.

While preferred embodiments of the present invention have been shown and described, it will be understood by those skilled in the art that various changes and modifications could be made without varying from the scope of the present invention.

What is claimed is:

1. In a radiology protective garment having radiation shielding material therein, the improvement comprising:

a wide support member having at least a portion extending across the back of the garment, said support member being positioned on said garment and being flexible and resilient in orthogonal directions to conform to the three-dimensional contour of the back of the wearer of the garment, the garment having front and back panels connected by vertical seams and wherein said support element is a band on the inside of a back panel of the garment, said band having substantially vertical ends which are connected to said vertical seams between front and back panels of the garment, the relaxed horizontal length of said band being less than the back panel distance between the same seams such that application of the garment to the body of the wearer causes the support element to be attached across and conform to the back of a person wearing the garment, to substantially release the weight of the garment from the shoulders and distribute the weight across the back.

2. The garment of claim 1 wherein said support element has a vertical width of about 4-8 inches.

3. The garment of claim 1 having shoulder portions, wherein said support member has upwardly extending portions that extend up from said portion that covers the small of the back of the wearer to the shoulder portions of the garment.

4. The garment of claim 1 wherein said support member is made of neoprene.

5. The garment of claim 1 wherein said support member is made of neoprene foam with a stretch nylon laminated cover.

6. The garment of claim 1 wherein said support member is made of an elastic material having similar moduli of elasticity in at least two directions.

7. The garment of claim 1 further comprising a neck protection portion extending from the front panel to cover a thyroid gland of the wearer.

8. A radiology protective garment containing shielding material therein comprising a back panel, a first front panel and a second front panel, releasable separator means provided for attaching the front panels together and, resilient support means having a first end connected at a first interior side of the back panel and a second end connected at a second interior side of the back panel, the support means extendable across the width of the back panel, the horizontal length of the support means in an unstressed state being less than the width of the back panel such that when the first and second front panels are attached, the support means is stretched across and conforms to the back of a person wearing the garment.

9. The garment of claim 8 further comprising neck protection portions extending from the first and second front panels.

10. The garment of claim 8 wherein said support element has a vertical width of about 4-8 inches.

11. The garment of claim 8 wherein said support member is made of an elastic material having similar moduli of elasticity in at least two directions.

12. A radiology protective garment having a front panel incorporating at least one leaded panel therein, first and second back panels attached to said front panel, each back panel attached at a shoulder seam and a side seam to the front panel and each back panel being wide and stretchable from the shoulder seams across the back of a wearer and being resilient in a longitudinal direction as well as in a direction perpendicular thereto for conforming to the back of a person wearing the garment, the back panels crossed across the back and having non-resilient portions extendable to meet and engage each other having means for attaching the non-resilient portions to eachother at the to hold the front panel against the body wherein the attachment of the non-resilient portions causes the stretchable back panels to stretch and release substantial weight from the shoulders and distribute the weight across the back.

* * * * *